United States Patent
Maruhata et al.

(10) Patent No.: US 8,758,320 B2
(45) Date of Patent: Jun. 24, 2014

(54) DISPOSABLE DIAPER HAVING A FASTENING TAPE WITH STEPWISE ADJUSTABLE LENGTH

(75) Inventors: Kazuya Maruhata, Tsurugi-cho (JP); Hironobu Yokokawa, Tsurugi-cho (JP)

(73) Assignee: Livedo Corporation, Shikokuchuo-shi (JP)

( * ) Notice: Subject to any disclaimer, the term of this patent is extended or adjusted under 35 U.S.C. 154(b) by 367 days.

(21) Appl. No.: 13/202,057

(22) PCT Filed: Feb. 26, 2010

(86) PCT No.: PCT/JP2010/053696
§ 371 (c)(1),
(2), (4) Date: Aug. 17, 2011

(87) PCT Pub. No.: WO2010/106926
PCT Pub. Date: Sep. 23, 2010

(65) Prior Publication Data
US 2011/0301563 A1    Dec. 8, 2011

(30) Foreign Application Priority Data

Mar. 17, 2009   (JP) ................................. 2009-064736

(51) Int. Cl.
*A61F 13/58*   (2006.01)
*A61F 13/62*   (2006.01)
*A61F 13/60*   (2006.01)

(52) U.S. Cl.
USPC ............................ 604/389; 604/390; 604/391

(58) Field of Classification Search
USPC ................................................ 604/389–391
See application file for complete search history.

(56) References Cited

U.S. PATENT DOCUMENTS 4,237,890 A    12/1980  Laplanche
5,281,209 A *   1/1994  Osborn et al. ............ 604/385.04
(Continued)

FOREIGN PATENT DOCUMENTS

EP    0757550 A1    2/1997
EP    1962762 A1    9/2008
(Continued)

OTHER PUBLICATIONS

International Search Report for PCT/JP2010/053696, mailing date of Aug. 30, 2010.
(Continued)

*Primary Examiner* — Susan Su
(74) *Attorney, Agent, or Firm* — Westerman, Hattori, Daniels & Adrian, LLP

(57) ABSTRACT

A disposable diaper comprising: a fastening tape having a tab part which is formed at one end of a tape substrate, a fixing part which is formed at the other end of the tape substrate, and an adjustment part which is formed between the tab part and the fixing part; a diaper main body having a front part, a back part and a crotch part positioned between the front part and the back part; wherein an attachment is fixed to the tab part, the fastening tape is attached to a side end of the front or back part of the diaper main body at the fixing part, the adjustment part is folded and temporarily joined to the diaper main body and/or the fastening tape at a joining part, and a length of the fastening tape between the attachment and the joining part which is the nearest to the attachment is longer than a length between an outer edge of the diaper main body and the joining part which is the nearest to the attachment. According to the disposable diaper of the present invention, the length of the fastening tape is adjustable in accordance with a size of a wearer's waist, and hence the disposable diaper of one size can be worn by people of various body types.

15 Claims, 13 Drawing Sheets

(56) References Cited

U.S. PATENT DOCUMENTS

| | | | |
|---|---|---|---|
| 5,304,162 A | | 4/1994 | Kuen |
| 5,730,739 A | * | 3/1998 | Lavash et al. .................. 604/387 |
| 7,867,213 B2 | | 1/2011 | Bandorf et al. |
| 8,419,704 B2 | * | 4/2013 | Magnusson et al. .......... 604/389 |
| 8,496,640 B2 | * | 7/2013 | Molander ..................... 604/389 |
| 2001/0034512 A1 | | 10/2001 | Karlsson et al. |
| 2004/0170794 A1 | | 9/2004 | Verhaert |
| 2004/0236301 A1 | | 11/2004 | Wendelstorf et al. |
| 2008/0033389 A1 | | 2/2008 | Bandorf et al. |
| 2009/0043275 A1 | | 2/2009 | Perneborn |

FOREIGN PATENT DOCUMENTS

| | | | |
|---|---|---|---|
| JP | 2003-265527 A | | 9/2003 |
| JP | 2004-321269 A | | 11/2004 |
| JP | 2004-538089 A | | 12/2004 |
| JP | 2008-515497 A | | 5/2008 |

OTHER PUBLICATIONS

Singapore Written Opinion dated Nov. 9, 2012, issued in corresponding Singapore Patent Application No. 201106608-1.

Mexican Office Action dated Aug. 22, 2013, isssued in corresponding Mexican Patent Application No. MX/a/2011/009637, w/English translation.

Chinese Office Action dated Sep. 12, 2013, issued in corresponding Chainese Patent Application No. 201080009682.2, w/English translation.

Chinese Office Action dated Feb. 26, 2013, issued in corresponding Chinese Patent Application No. 201080009682.2, with English translation (18 pages).

Japanese Office Action dated Apr. 16, 2013, issued in corresponding Japanese Patent Application No. 2009-064736, with English translation (7 pages).

Australian Office Action dated Apr. 15, 2013, issued in corresponding Australian Pateant Application No. 2010225865 (3 pages).

European Office Action dated Jan. 29, 2014, issued in European Patent Application No. 10715364.5 (8 pages).

Chinese Office Action dated Feb. 24, 2014, issued in Chinese Patent Application No. 201080009682.2, w/English translation (22 pages).

Mexican Office Action dated Feb. 17, 2014, issued in Mexican Patent Application No. MX/a/2011/009637, w/English translation (11 pages).

* cited by examiner

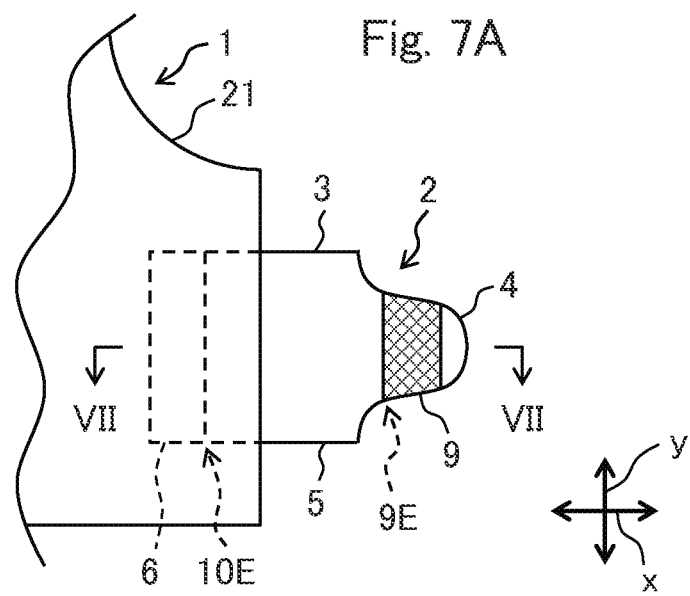
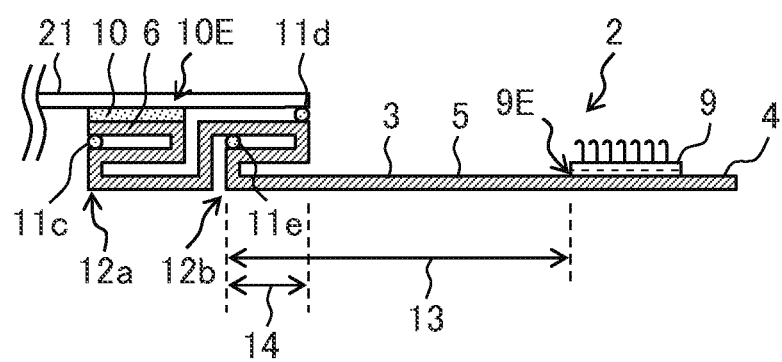

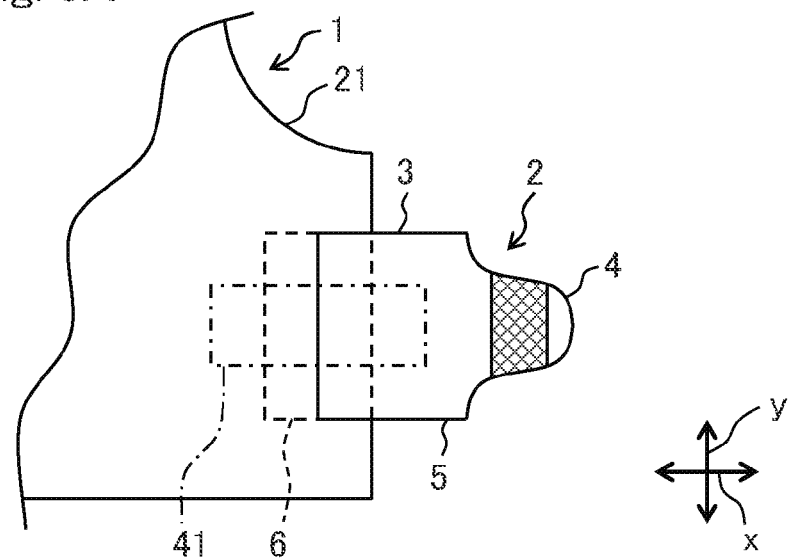
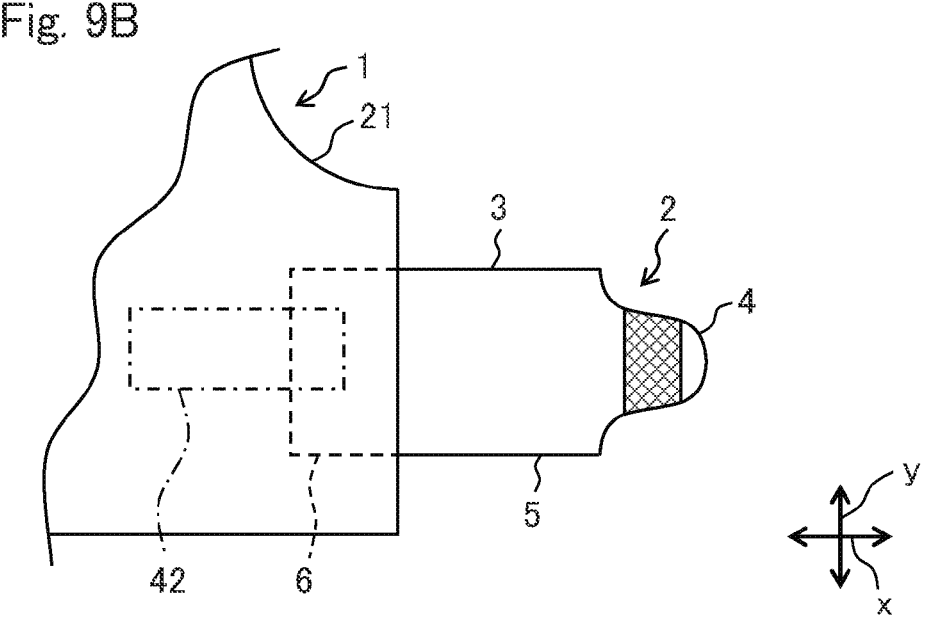

DISPOSABLE DIAPER HAVING A FASTENING TAPE WITH STEPWISE ADJUSTABLE LENGTH

TECHNICAL FIELD

The present invention relates to a disposable diaper provided with a fastening tape.

BACKGROUND ART

Conventionally, there is known a disposable diaper which is provided with a fastening tape. For example, Japanese Laid-Open Patent Publication No. 2004-538089 (Patent Literature 1) discloses a disposable diaper in which a fastening tape having an attachment is folded into a Z shape so that the attachment is detachably joined to a diaper main body. In the Patent Literature 1, the fastening tape is folded for temporarily joining the attachment to the diaper main body, prior to use of the disposable diaper.

CITATION LIST

Patent Literature

Patent Literature 1
Japanese Laid-Open Patent Publication No. 2004-538089

SUMMARY OF INVENTION

Technical Problem

Since people of various body types use disposable diapers, disposable diapers are commercially available in many sizes that fit to the body types of wearers. In particular, when adults use disposable diapers, the difference between the body types of wearers is great, as compared to that in the case of babies. However, for example, in care facilities and hospitals, preparation of disposable diapers with various sizes requires a large storage area for the diapers, and is not preferred in terms of cost. In addition, when a wearer, whose balance between the sizes of the waist and the hip is different from that of standard body types, uses a standard disposable diaper, the wearer may not obtain a comfortable feel of wearing.

The present invention has been achieved in view of the above circumstances, and an object of the present invention is to provide a disposable diaper having a fastening tape whose length is adjustable in accordance with a size of a wearer's waist.

Solution to Problem

A disposable diaper of the present invention which solves the above problems comprises: a fastening tape having a tab part which is formed at one end of a tape substrate, a fixing part which is formed at the other end of the tape substrate, and an adjustment part which is formed between the tab part and the fixing part; a diaper main body having a front part, a back part and a crotch part positioned between the front part and the back part; wherein an attachment is fixed to the tab part, the fastening tape is attached to a side end of the front or back part of the diaper main body at the fixing part, the adjustment part is folded and temporarily joined to the diaper main body and/or the fastening tape at a joining part, and a length of the fastening tape between the attachment and the joining part which is the nearest to the attachment is longer than a length between an outer edge of the diaper main body and the joining part which is the nearest to the attachment.

The disposable diaper of the present invention can be worn in the state where the adjustment part is unfolded by releasing a temporarily joining of the adjustment part at the joining part as well as in the state where the adjustment part is folded. Therefore, the disposable diaper of one size can be worn by people of various body types by adjusting the length of the fastening tape in accordance with the size of a wearer's waist.

A joining strength at the joining part is preferably lower than rupture strengths of the diaper main body and the fastening tape. When the joining strength at the joining part is lower than the rupture strengths of the diaper main body and the fastening tape, the adjustment part of the fastening tape is easily unfolded without breaking the diaper main body and the fastening tape.

The joining part is preferably formed by an adhesive or heat-sealing. When the joining part is formed by an adhesive, it becomes easy to form the bonding part into an optional pattern, and hence the joining part is easily formed. When the joining part is formed by heat-sealing, the fastening tape is relatively rigidly joined to the diaper main body or itself, and hence the joining part becomes durable.

The joining part may be provided discontinuously. When the joining part is provided discontinuously, the fastening tape is hardly broken from the joining part in releasing the temporary joining at the joining part.

The adjustment part preferably extends from an outer border of the fixing part. When the adjustment part extends from the outer border of the fixing part, the fastening tape is more rigidly fixed to the diaper main body, especially in using in the state where the adjustment part is unfolded, relative to the case of the adjustment part extending from an inner border of the fixing part. Therefore, handleability of the disposable diaper improves.

The tab part may be turned back by folding the adjustment part at a fold so that the attachment is inside the fold, and the attachment may be joined to the adjustment part. In this case, prior to use of the disposable diaper, exposure of the attachment is suppressed. Thus, the attachment is less likely to be unintentionally joined to another member, resulting in excellent in handleability.

Advantageous Effects of Invention

In the disposable diaper of the present invention, the length of the fastening tape is adjustable in accordance with a size of a wearer's waist, and hence the disposable diaper of one size can be worn by people of various body types.

BRIEF DESCRIPTION OF DRAWINGS

FIG. 1 shows an example of a fastening tape used for the present invention.

FIG. 2 shows the fastening tape in the state where the adjustment part of the fastening tape in FIG. 1 is unfolded.

FIG. 3 shows the fastening tape in the state where the tab part of the fastening tape in FIG. 1 is turned back.

FIG. 4 shows the fastening tape in the state where the fastening tape in FIG. 3 is folded along an outer edge of a diaper main body.

FIG. 5 shows another example of a fastening tape used for the present invention.

FIG. 6 shows another example of a fastening tape used for the present invention.

FIG. 7 shows another example of a fastening tape used for the present invention, FIG. 7A shows a plain view, and FIG. 7B shows a cross sectional view along line VII-VII in FIG. 7A.

FIG. 9A and FIG. 9B show examples of a cutting location in obtaining a test piece for measuring a joining strength at a joining part and a rupture strength of a diaper main body.

DESCRIPTION OF EMBODIMENTS

Figure 1A:
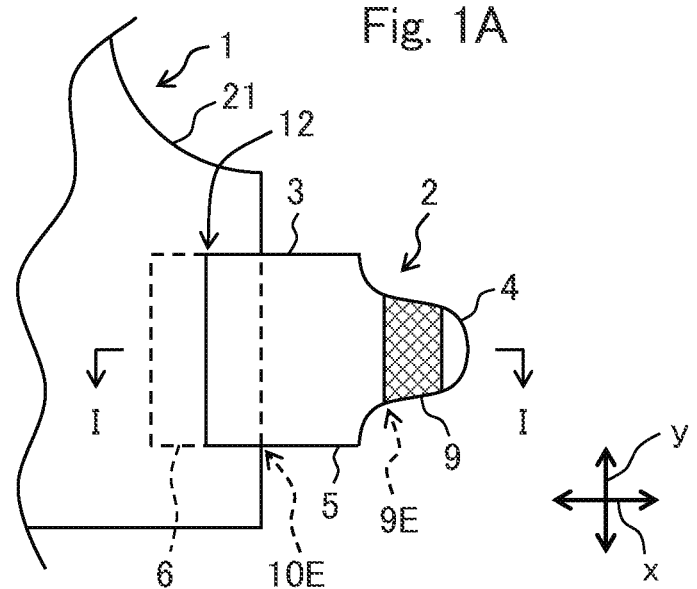
FIG. 1A shows a plain view.

A disposable diaper of the present invention comprises a diaper main body and a fastening tape. The diaper main body has a front part, a back part and a crotch part positioned between the front part and the back part, and the fastening tape is attached to a side end of the front or back part of the diaper main body. Here, a part applied to an abdomen side of a wearer is called the front part, a part applied to a buttocks side of the wearer is called the back part, and a part positioned between the front part and the back part and applied to a crotch of the wearer is called the crotch part, in a state of wearing the disposable diaper.

The fastening tape is attached to at least one part selected from the group consisting of a left side end of the front part, a right side end of the front part, a left side end of the back part, and a right side end of the back part. Preferably, a pair of the fastening tapes is attached to the left and right side ends of the front part, or the left and right side ends of the back part.

The diaper main body may comprise, for example, a laminate including a liquid-permeable top sheet, a liquid-impermeable back sheet and an absorbent core interposed therebetween, wherein the laminate having a front part, a back part and a crotch part therebetween. Also, the diaper main body may comprise an outer sheet having a front part, a back part and a crotch part therebetween; and an absorbent main body including a liquid-permeable top sheet, a liquid-impermeable back sheet and an absorbent core interposed therebetween, wherein the absorbent main body is disposed on an inner surface, that faces a wearer in wearing, at the crotch part of the outer sheet.

The fastening tape comprises a tape substrate and an attachment. The fastening tape has a tab part which is formed at one end of the tape substrate, a fixing part which is formed at the other end of the tape substrate, and an adjustment part which is formed between the tab part and the fixing part.

The tab part is a part formed at one end of the tape substrate, and the attachment is fixed to the tape substrate at the tab part. The attachment is preferably fixed to only one surface of the tape substrate. In addition, the attachment is preferably fixed to only at the tab part.

Examples of the attachment include a hook member and a loop member of a hook-and-loop fastener; and an adhesive such as an adhesive tape and an adhesive layer; and the like. As the hook member, a member having hooks of, for example, an anchor shape, a hook shape, a mushroom shape, or the like may be used. As the loop member, a member in which a loop structure is formed on a surface thereof may be employed, and a nonwoven fabric, a woven fabric, a knitted fabric, a composite material of a plastic film having a nonwoven fabric, a woven fabric on a surface, or the like can be used.

The fixing part is a part which is formed at the other end of the tape substrate and is attached to the diaper main body. The fixing part is fixed to the diaper main body at a bonding part. The bonding part is formed, for example, by a heretofore known adhesive means such as an adhesive agent, heat-sealing, ultrasonic bonding or the like. The fixing part of the tape substrate may be attached, for example, between two components constituting the diaper main body, or on one surface of a component constituting the diaper main body. The fixing part of the tape substrate is attached, for example, between the top sheet and the back sheet, or on one surface of the outer sheet.

The adjustment part is a part formed between the tab part and the fixing part. The adjustment part is a part between the tab part and the fixing part, corresponding to a part which is not attached to the diaper main body and to which the attachment is not fixed. The fixing part and the adjustment part are delimited at a side edge of the bonding part at which the fastening tape is attached to the diaper main body. The tab part and the adjustment part are delimited at a side edge of the attachment. Here, the side edges means edges with respect to a width direction of the disposable diaper.

A front-back direction means a direction extending from the front part toward the back part of the disposable diaper. The width direction means a direction orthogonal to the front-back direction on the same plane as the disposable diaper. That is, the width direction corresponds to a direction extending from a right side to a left side of a wearer and vice versa when the wearer wears the disposable diaper.

The adjustment part is folded and temporarily joined to the diaper main body and/or the fastening tape at a joining part. Details of folding manner of the adjustment part and providing the joining part are explained below.

A shape of the fastening tape is not particularly limited. The shape of the fastening tape may be, for example, polygonal such as rectangular, oval, or the like, and an elongated shape is preferable. The fastening tape may be formed in such a manner that one end of the tape substrate at which the tab part is formed or the other end of the tape substrate at which the fixing part is formed has, for example, a straight linear or meandering outline. One end of the tape substrate at which the tab part is formed has preferably a meandering outline in view of manufacturing efficiency and easily pinching of the tab part. On the other hand, the other end of the tape substrate at which the fixing part is formed has preferably a straight linear outline.

Figure 1B:
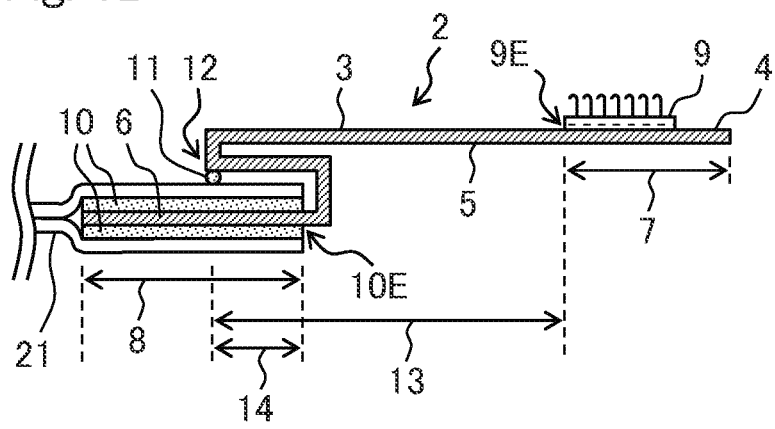
FIG. 1B shows a cross sectional view along line I-I in FIG. 1A.

An example of the fastening tape used for the present invention is shown in FIG. 1. FIG. 1A shows a plain view a fastening tape, and FIG. 1B shows a cross sectional view along line I-I of FIG. 1A. A fastening tape 2 has a tab part 4 which is formed at one end of a tape substrate 3, a fixing part 6 which is formed at the other end of the tape substrate 3, and a adjustment part 5 which is formed between the tab part 4 and the fixing part 6.

The attachment 9 is fixed to the tab part 4. The tab part 4 and the adjustment part 5 are delimited at a side edge 9E of the attachment 9, and the tab part 4 is the part of the fastening tape 2 in the range indicated by an arrow 7.

In FIG. 1, a hook member is provided as the attachment 9. The hook member comprises a base part and a hook part, and the hook part is composed of a plurality of hooks projected from one surface of the base part. The opposite surface of the base part, that is the opposite surface of the surface with the hook part, is joined to the tape substrate 3.

The fixing part 6 is fixed to the diaper main body 21 at a bonding part 10. In FIG. 1, the fixing part 6 is attached between two sheets constituting the diaper main body 21. The fixing part 6 and the adjustment part 5 are delimited at a side edge 10E of the bonding part 10, and the fixing part 6 is the part of the fastening tape 2 in the range indicated by an arrow 8.

The adjustment part 5 is formed between the tab part 4 and the fixing part 6, and is a part of the fastening tape 2 other than the parts in the ranges indicated by the arrows 7 and 8. In FIG. 1, the adjustment part 5 extends from an outer border of the fixing part 6. Here, the outer border means an outer border with respect to the width direction x of the disposable diaper 1.

The adjustment part 5 is folded and temporarily joined to the diaper main body 21 at a joining part 11. In FIG. 1, the adjustment part 5 is folded so that the fastening tape 2 is formed into a Z shape in cross section. The adjustment part 5 is folded inwardly at a boundary between the adjustment part 5 and the fixing part 6, that is, at the side edge 10E of the bonding part 10, and the inwardly-folded adjustment part 5 is folded outwardly, thereby forming an inner fold line 12 at the adjustment part 5. Here, the terms "inwardly" and "outwardly" means directions along the width direction x of the disposable diaper 1. The adjustment part 5 is folded and temporarily joined to the diaper main body 21 at the joining part 11 at the inner fold line 12.

A length of the fastening tape 2 between the attachment 9 and the joining part 11, that is the length corresponding to the length of the arrow 13, is longer than a length between an outer edge of the diaper main body 21 and the joining part 11, that is the length corresponding to the length of the arrow 14. Thus, when the fastening tape 2 is used, the attachment 9 is located entirely outside the diaper main body 21 even in a state where the adjustment part 5 is folded. Therefore, even in the state where the adjustment part is folded, the disposable diaper of the present invention can be worn by joining the fastening tape to a later-described attachment-receiving part. The fastening tape in the state where the adjustment part is folded is suitably used when a thin or small person wears the disposable diaper.

On the other hand, when an overweight or large person wears the disposable diaper of the present invention, the diaper may not sufficiently cover a waist of the wearer with the fastening tape in the state where the adjustment part is folded. Thus, there is the possibility that the fastening tape does not reach the later-described attachment-receiving part or a joining force of the fastening tape is weakened. In this case, it is preferred that the fastening tape is used after the temporary joining of the adjustment part at the joining part is released and the adjustment part is unfolded.

Figure 2A:
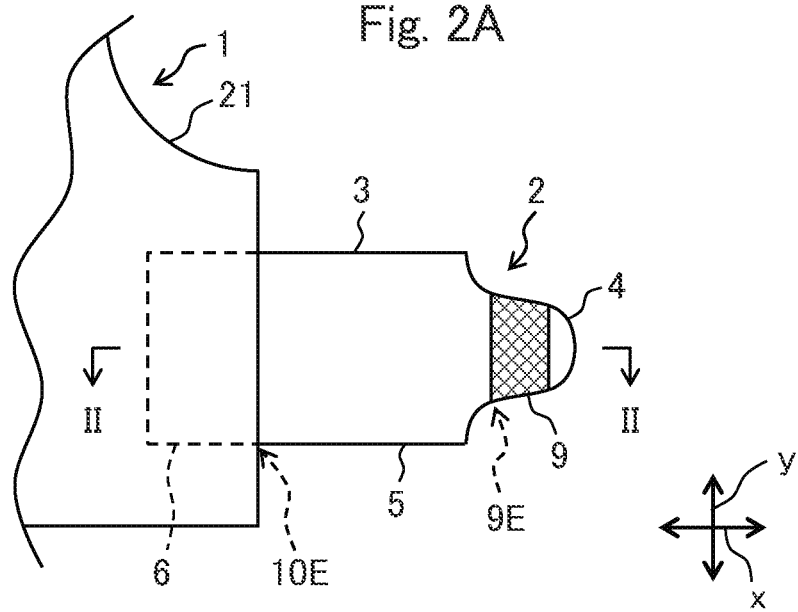
FIG. 2A shows a plain view.
Figure 2B:
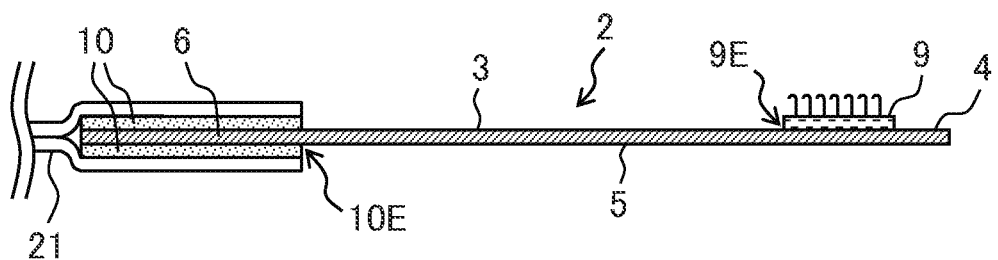
FIG. 2B shows a cross sectional view along line II-II in FIG. 2A.

FIG. 2 shows a state where the temporary joining of the adjustment part at the joining part is released in the fastening tape shown in FIG. 1. FIG. 2A shows a plan view of the fastening tape, and FIG. 2B shows a cross sectional view along line II-II of FIG. 2A. The fastening tape 2 is shifted from the state in FIG. 1 to the state in FIG. 2 by: releasing the temporary joining of the adjustment part 5 at the joining part 11 and; unfolding the adjustment part 5. The length of the fastening tape 2 with respect to the width direction x increases by unfolding the adjustment part 5. The fastening tape in the state where the adjustment part is unfolded is suitably used when an overweight or large person wears the disposable diaper.

As shown in FIGS. 1 and 2, the disposable diaper of the present invention comprises the fastening tape whose length is adjustable. Thus, by adjusting the length of the fastening tape in accordance with the size of a wearer's waist, people of various body types can wear the disposable diaper of one size.

In FIGS. 1 and 2, the fixing part 6 is provided so as to extend to the outer edge of the diaper main body 21, and the adjustment part 5 extends from the outer border of the fixing part 6. When the boundary between the fixing part 6 and the adjustment part 5 is located at about the outer edge of the diaper main body 21, the fastening tape and the diaper main body are easily handled together in the state where the adjustment part is unfolded, resulting in excellent in operability of the diaper in wearing or removing. The boundary between the fixing part 6 and the adjustment part 5 is preferably located within 15 mm from the outer edge of the diaper main body, and more preferably located within 10 mm from the outer edge of the diaper main body.

Prior to use of the disposable diaper of the present invention, the fastening tape may be folded back as appropriate. Prior to use of the disposable diaper, when the attachment is exposed, there is the possibility that the attachment is joined to or damages another member of the disposable diaper. Therefore, prior to use of the disposable diaper, preferably, the tab part is turned back by folding the adjustment part at a fold so that the attachment is inside the fold, and the attachment is detachably joined to the adjustment part. This will be described with reference to FIG. 3.

Figure 3A:
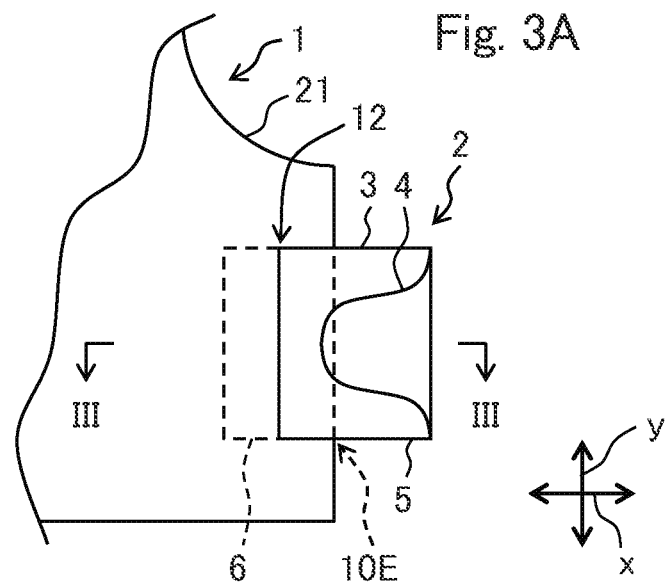
FIG. 3A shows a plain view.
Figure 3B:
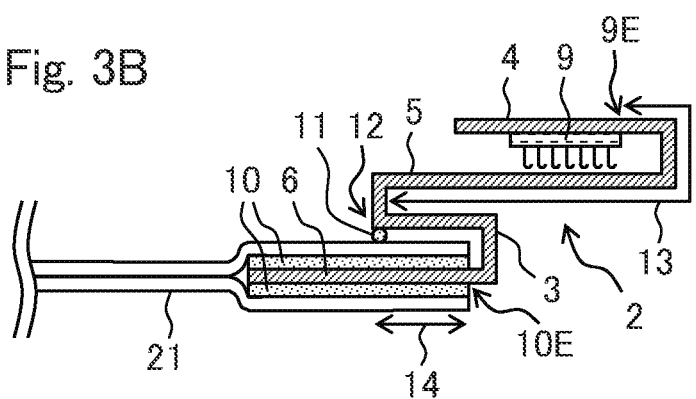
FIG. 3B shows a cross sectional view along line III-III in FIG. 3A.

FIG. 3 shows a state where the tab part is turned back in the fastening tape shown in FIG. 1. FIG. 3A shows a plan view of the fastening tape, and FIG. 3B shows a cross sectional view along line III-III FIG. 3A. In FIG. 3, the tab part 4 is turned back by folding the adjustment part 5 at a fold so that the attachment 9 is inside the fold, and the attachment 9 is joined to the adjustment part 5. When the attachment 9 is joined to the adjustment part 5 prior to use of the disposable diaper, exposure of the attachment 9 is suppressed. Thus, the attachment 9 is less likely to be unintentionally joined to another member, resulting in excellent in handleability. In addition, the attachment 9 is less likely to damage another member. In this case, a length of the tab part is preferably shorter than a length of the folded adjustment part. Here, the lengths of the tab part and the adjustment part means lengths with respect to the width direction x of the disposable diaper 1.

When the fastening tape 2 is folded at a part thereof nearer to the tab part 4 than the joining part 11 (the joining part nearest to the attachment in the case where there are two or more joining parts) as shown in FIG. 3, the length of the fastening tape 2 between the attachment 9 and the joining part 11 does not mean the shortest distance from the attachment 9 to the joining part 11, but means a path length of the fastening tape 2 from the attachment 9 to the joining part 11. The length between the outer edge of the diaper main body 21 and the joining part 11 means a length on the diaper main body 21, and specifically means a length from the outer edge of the diaper main body 21 to the projected position of the joining part 11 on the diaper main body 21. Thus, in FIG. 3 as well, the length between the attachment 9 and the joining part 11, that is the length corresponding to the length of the arrow 13, is longer than the length between the outer edge of the diaper main body 21 and the joining part 11, that is the length corresponding to the length of the arrow 14.

Figure 4A:
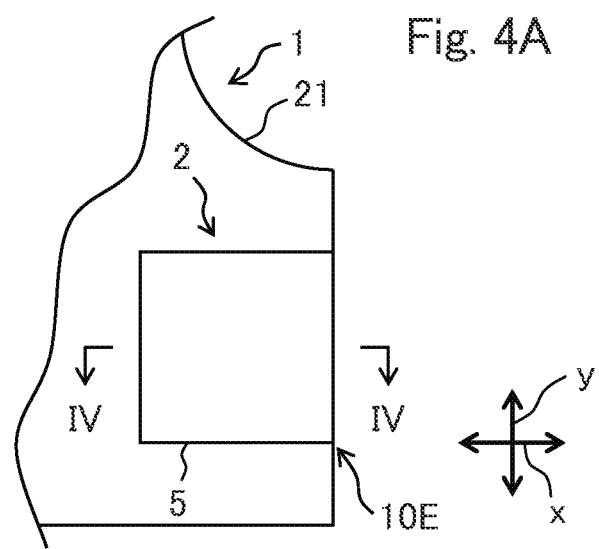
FIG. 4A shows a plain view.
Figure 4B:
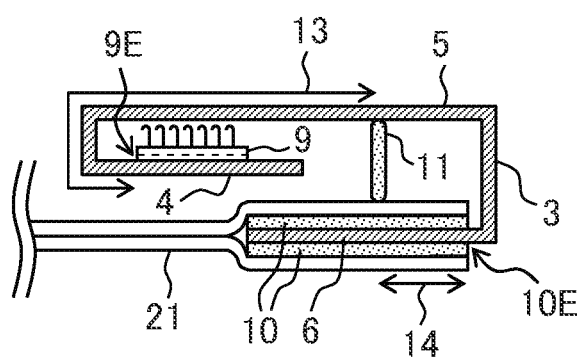
FIG. 4B shows a cross sectional view along line IV-IV in FIG. 4A.

In FIG. 4, the fastening tape 2 shown in FIG. 3 is folded along the outer edge of the diaper main body 21, whereby the fastening tape 2 is folded back on the diaper main body 21. FIG. 4A shows a plan view of the fastening tape, and FIG. 4B shows a cross sectional view along line Iv-Iv FIG. 4A. In the disposable diaper 1 of an unused state that it is just manufactured, the fastening tape 2 attached to the disposable diaper 1 is preferably in the state shown in FIG. 4, because the disposable diaper 1 becomes compact. In FIG. 4 as well, the length between the attachment 9 and the joining part 11, that is the length corresponding to the length of the arrow 13, is longer than the length between the outer edge of the diaper main body 21 and the joining part 11, that is the length corresponding to the length of the arrow 14.

The following will describe another embodiment of a fastening tape, which is different from the fastening tape shown in FIGS. 1 to 4.

Figure 5A:
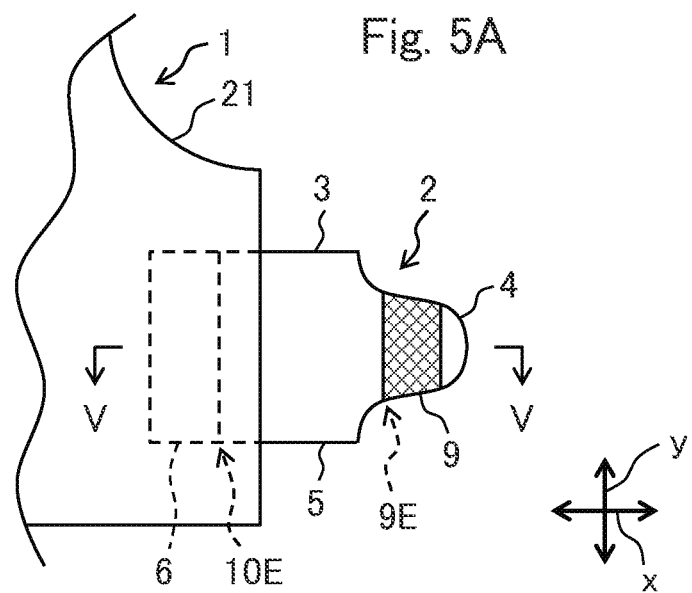
FIG. 5A shows a plain view.
Figure 5B:
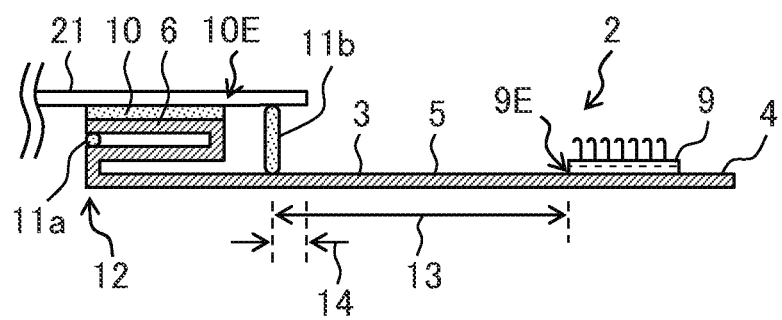
FIG. 5B shows a cross sectional view along line V-V in FIG. 5A.

FIG. 5 shows a fastening tape that differs from the fastening tape shown in FIG. 1, in the manner where the fixing part is attached to the diaper main body; and in the number of joining parts. FIG. 5A shows a plan view of a fastening tape, and FIG. 5B shows a cross sectional view along line V-V of FIG. 5A. In FIG. 5, the fastening tape 2 is attached to a surface of one sheet constituting the diaper main body 21 at the fixing part 6. The fixing part 6 is provided so as not to extend to the outer edge of the diaper main body 21.

The adjustment part 5 extends from the outer border of the fixing part 6. The adjustment part 5 is folded inwardly at the boundary between the adjustment part 5 and the fixing part 6, that is, at the side edge 10E of the bonding part 10, and the inwardly-folded adjustment part 5 is folded outwardly, thereby forming an inner fold line 12 at the adjustment part 5. In FIG. 5, the adjustment part 5 is folded and temporarily joined to both the fastening tape 2 at a joining part 11a at the inner fold line 12 and the diaper main body 21 at a joining part 11b outside the side edge 10E of the bonding part 10.

In the fastening tape, the joining parts may be provided at two or more locations as shown in FIG. 5. By providing the joining parts at two or more locations, the fastening tape is maintained more stably in the state where the adjustment part is folded, and hence the handleability of the fastening tape improves. In particular, when the joining part which is the nearest to the attachment is disposed within 15 mm (more preferably within 10 mm) from the outer edge of the diaper main body, the fastening tape and the diaper main body are easily handled together in the state where the adjustment part is folded, resulting in excellent in operability of the diaper in wearing or removing. Here, the joining part which is the nearest to the attachment means the joining part provided so as to be the nearest on the path of the fastening tape to the attachment, and is not necessarily the joining part located so as to be nearest to the attachment in a linear distance.

When the joining parts are provided at two or more locations, the length between of the fastening tape 2 between the attachment 9 and the joining part 11b which is the nearest to the attachment 9 (the length corresponding to the length of the arrow 13) is longer than the length between the outer edge of the diaper main body 21 and the joining part 11b which is the nearest to the attachment 9 (the length corresponding to the length of the arrow 14). Therefore, in the fastening tape 2, the attachment 9 is located entirely outside the diaper main body 21 even in the state where the adjustment part 5 is folded, resulting in excellent in handleability of the fastening tape in wearing the diaper.

Figure 6A:
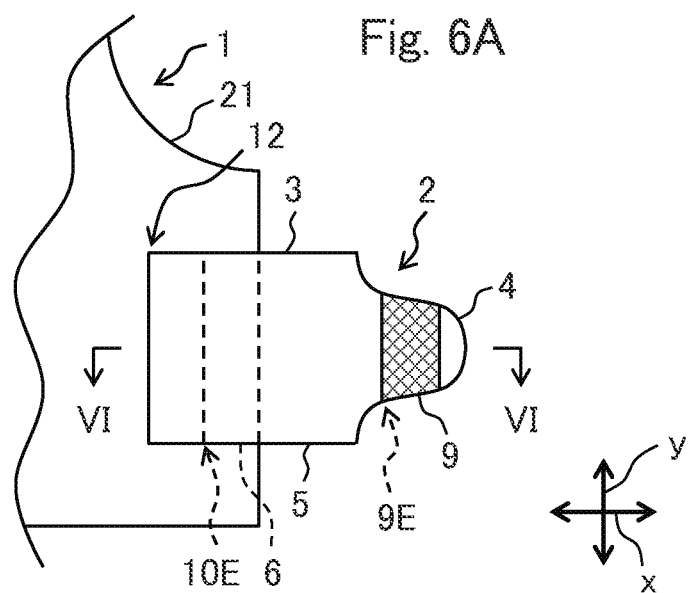
FIG. 6A shows a plain view.
Figure 6B:
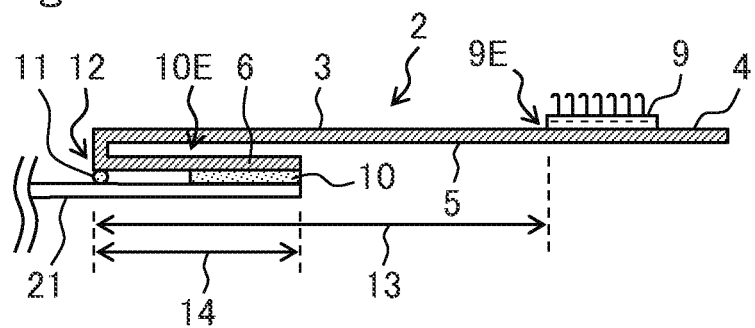
FIG. 6B shows a cross sectional view along line VI-VI in FIG. 6A.

FIG. 6 shows a fastening tape that differs from the fastening tape shown in FIG. 1 in the manner where the fixing part is attached to the diaper main body and in the manner where the adjustment part is folded. FIG. 6A shows a plan view of the fastening tape, and FIG. 6B is a cross sectional view along line VI-VI of FIG. 6A.

In FIG. 6, the fastening tape 2 is attached to a surface of one sheet constituting the diaper main body 21 at the fixing part 6. The adjustment part 5 extends from an inner border of the fixing part 6 unlike to the fastening tape shown in FIG. 1. The adjustment part 5 is folded so that the fastening tape 2 is formed into a C shape in cross section. The adjustment part 5 extending inward from the inner border of the fixing part 6 is folded outwardly, thereby forming an inner fold line 12 at the adjustment part 5. In FIG. 6, the adjustment part 5 is folded and temporarily joined to the diaper main body 21 at the joining part 11 at the inner fold line 12.

In the fastening tape shown in FIG. 6 as well, the length between the attachment 9 and the joining part 11, that is the length corresponding to the length of the arrow 13, is longer than the length between the outer edge of the diaper main body 21 and the joining part 11, that is the length corresponding to the length of the arrow 14. Therefore, in the fastening tape 2, the attachment 9 is located entirely outside the diaper main body 21 even in the state where the adjustment part 5 is folded, resulting in excellent in handleability of the fastening tape in wearing the diaper.

FIG. 6 shows the embodiment where the adjustment part 5 extends from the inner border of the fixing part 6, however, it is more preferred that the adjustment part 5 extends from the outer border of the fixing part 6 as shown in FIGS. 1 to 5. During use of the diaper, the fastening tape 2 is subjected to a force so as to be pulled outwardly. In the case where the adjustment part 5 extends from the outer border of the fixing part 6, a shear force is applied between the fixing part 6 and the diaper main body 21. On the other hand, in the case where the adjustment part 5 extends from the inner border of the fixing part 6, a peel force is applied between the fixing part 6 and the diaper main body 21. When the condition of bonding the fixing part 6 to the diaper main body 21 at the bonding part 10 is the same, the bonding of the fixing part 6 to the diaper main body 21 is more resistant to the shear force than to the peel force. Thus, when the adjustment part extends from the outer border of the fixing part, the fastening tape is more rigidly fixed to the diaper main body, especially in the case where the adjustment part is unfolded, and hence handleability of the disposable diaper improves.

In FIGS. 1 to 6, the adjustment part is folded so that the fastening tape is formed into a Z or C shape in cross section, however, the number of times of folding the adjustment part may be increased. For example, the adjustment part may be folded so that the fastening tape is formed into a Σ shape in cross section, or the adjustment part may be folded so that the fastening tape is formed into a shape in which Z letters are stacked in cross section.

FIG. 7 shows a fastening tape that further differs from the fastening tape described above in the manner where the adjustment part is folded. FIG. 7A shows a plan view of the fastening tape, and FIG. 7B shows a cross sectional view along line VII-VII of FIG. 7A. In FIG. 7, the fastening part is folded so that a Z shape is aligned in the width direction x of the disposable diaper 1.

The adjustment part 5 extends from the outer border of the fixing part 6. The adjustment part 5 is folded inwardly at the boundary between the adjustment part 5 and the fixing part 6, that is, at the side edge 10E of the bonding part 10, and the inwardly-folded adjustment part 5 is folded outwardly, thereby forming a first inner fold line 12a. The adjustment part 5 is temporarily joined to the fastening tape 2 at a joining part 11c at the inner fold line 12a. The outwardly-folded adjustment part 5 is further folded inwardly at a position outside the side edge 10E of the bonding part 10, and is temporarily joined to the diaper main body 21 at a joining part 11d at the position where the adjustment part 5 is folded inwardly outside the side edge 10E of the bonding part 10. The inwardly-folded adjustment part 5 is further folded outward outside the joining part 11c, thereby forming a second inner fold 12b. The adjustment part 5 is also temporarily joined to the fastening tape 2 at a joining part 11e at the inner fold line 12b.

In the fastening tape shown in FIG. 7, the joining part which is the nearest to the attachment 9 is the joining part 11e. In this case, the length of the fastening tape 2 between the attachment 9 and the joining part 11e which is the nearest to the attachment 9 (the length corresponding to the length of the arrow 13) is longer than the length between the outer edge of the diaper main body 21 and the joining part 11e which is the nearest to the attachment 9 (the length corresponding to the length of the arrow 14). Therefore, in the fastening tape 2, the attachment 9 is located entirely outside the diaper main body 21 even in the state where the adjustment part 5 is folded multiple times, resulting in excellent in handleability of the fastening tape in wearing the diaper.

As described above, when the adjustment part is folded so as to form the inner fold lines at two or more locations, the length of the fastening tape becomes adjustable in a stepwise manner. For example, in FIG. 7, by releasing the temporary joining at the joining part 11e, the fastening tape is unfolded as a first step, whereby the length of the fastening tape increases. Besides, by releasing the temporary joining at the joining parts 11d and 11c, the fastening tape is unfolded as a second step, whereby the length of the fastening tape further increases. Thus, when the adjustment part is folded so as to form the inner fold lines at two or more locations, the length of the fastening tape becomes more flexibly adjustable so as to fit to the body form of a wearer.

Figure 8:
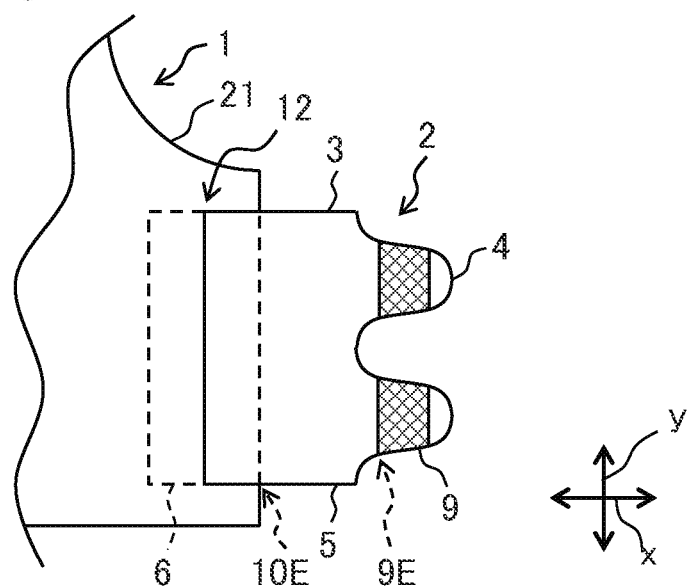
FIG. 8 shows another example of a fastening tape used for the present invention.

FIG. 8 shows a fastening tape that differs from the fastening tape shown in FIG. 1 in the shape of the tape substrate where the tab part is formed. In FIG. 8, one end of the tape substrate 3 in which the tab part 4 is formed has a meandering outline with more meandering numbers than in FIG. 1. The fastening tape shown in FIG. 8 is preferable, because the attachments 9 fixed on two sites makes it easy to adjust a size around waist and trunk so as to fit the body form of a wearer in wearing a diaper.

The joining part is formed by an adhesive, heat-sealing, ultrasonic bonding, or the like, and preferably formed by an adhesive or by heat-sealing. When the joining part is formed by an adhesive, it becomes easy to form the bonding part into an optional pattern, such as a line pattern, a dot pattern, and a spiral pattern as a manufacturer wants, and hence the joining part is easily formed. When the joining part is formed by heat-sealing, the fastening tape is relatively rigidly joined to the diaper main body or itself, and hence the joining part becomes durable.

The joining part may be provided continuously or discontinuously, however, the joining part is preferably provided discontinuously. When the joining part is provided discontinuously, a joining strength of the entire joining part can be decreased while increasing a joining strength at a part where the adjustment part is actually joined. Therefore, the fastening tape is hardly broken from the joining part when the temporary joining of the adjustment part at the joining part is released and the fastening tape is unfolded. In particular, when the joining part is formed by heat-sealing, the part that has been subjected to heat-sealing is joined relatively rigidly, and hence it is preferred that the joining part is provided discontinuously.

The joining strength at the joining part is preferably lower than rupture strengths of the diaper main body and the fastening tape. When the joining strength at the joining part is lower than the rupture strengths of the diaper main body and the fastening tape, the adjustment part of the fastening tape is easily unfolded without breaking the diaper main body and the fastening tape. Here, the rupture strength indicates the lower strength out of the rupture strength of the diaper main body and the rupture strength of the fastening tape.

The joining strength and the rupture strength are measured as follows. A test piece for measuring each strength is cut off from the disposable diaper so as to have a size of 50 mm×120 mm to 150 mm. In cutting off the test piece from the disposable diaper, the test piece is cut off so as to have a length of 120 mm to 150 mm in the width direction x of the disposable diaper and a length of 50 mm in the front-back direction y of the disposable diaper.

A test piece for measuring the joining strength is prepared by cutting the fastening tape, in the state where the adjustment part of the fastening tape is folded, so that the joining part is located at about the center of the test piece. In cutting off the test piece, the diaper main body may also be cut simultaneously. FIG. 9A shows an example of a cutting location in obtaining the test piece for measuring the joining strength from the disposable diaper shown in FIG. 1. In order to obtain the test piece for measuring the joining strength, a portion surrounded by a region 41 may be cut off as shown in FIG. 9A, for example.

A test piece for measuring the rupture strength is prepared by cutting the diaper main body in the state where the adjustment part of the fastening tape is unfolded. In cutting off the test piece, the fastening tape may also be cut simultaneously; however, when the absorbent material is also cut simultaneously, the absorbent material is removed from the test piece. In preparing the test piece for measuring the rupture strength, the diaper main body is preferably cut so that the test piece does not include the fastening tape and the absorbent material as much as possible. When the diaper main body is formed, for example, from two sheets bonded to each other, a piece of two sheets bonded to each other is used as the test piece. FIG. 9B shows a cutting location in obtaining the test piece for measuring the rupture strength from the disposable diaper shown in FIG. 2. In order to obtain the test piece for measuring the rupture strength, a portion surrounded by a region 42 may be cut off as shown in FIG. 9B, for example.

Figure 10:
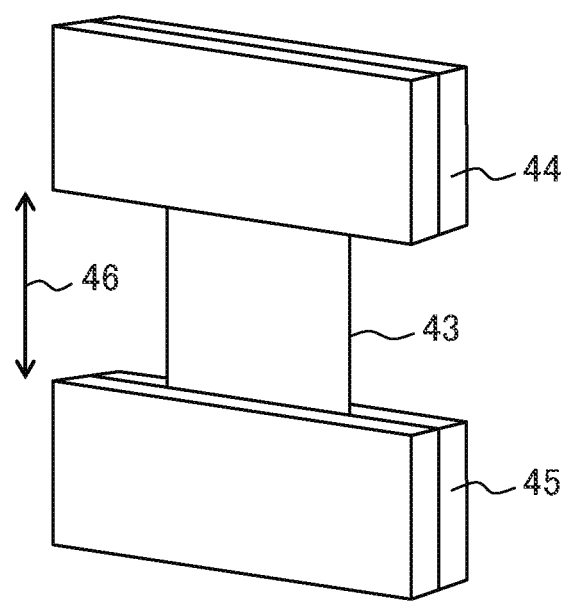
FIG. 10 shows a method for measuring a joining strength at a joining part and a rupture strength of a diaper main body.

Each strength is measured by pulling the test piece with a tensile strength tester. This will be described with reference to FIG. 10. A test piece 43 is fixed by clipping both ends in the longitudinal direction thereof with an upper chuck 44 and a lower chuck 45 of the tensile strength tester. The distance 46 between the upper chuck 44 and the lower chuck 45 is adjusted to be 100 mm. If a test piece having an insufficient length in the width direction of the disposable diaper is obtained, the distance 46 may be set to be shorter than 100 mm to measure the strength of each test piece. The positions of the upper chuck 44 and the lower chuck 45 are adjusted so that measurements are taken in a vertical direction. The test piece 43 is fixed to the chucks 44 and 45 so as not to be twisted or skewed.

After the test piece 43 is fixed to the chucks 44 and 45, the test piece 43 is pulled in the longitudinal direction of the test piece 43, that is, in the width direction of the disposable diaper, to measure the joining strength or the rupture strength.

In measuring the joining strength, the test piece is pulled until the joining is released. After the joining being released, the maximum value of the strength (peak strength) recorded during the measurement is regarded as a measurement result. In measuring the rupture strength, the test piece is pulled until it breaks. After the breakage, the maximum value of the strength (peak strength) recorded during the measurement is regarded as a measurement result. Each of the above measurements is taken using five test pieces, and an average value of the measurement results of the five measurements is referred to as the joining strength N1 or the rupture strength N2. When the diaper main body is composed of a same material on the right and left sides thereof, the test piece may be cut off from either side of the diaper main body; however, the five test pieces are preferably cut off from the same side.

For example, a sheet which is assumed to be used for a diaper main body was manufactured by bonding a back sheet and a side sheet to each other by a hot-melt adhesive to measure the rupture strength N2. Here, as the back sheet, a composite film was prepared by bonding an SMS nonwoven fabric having a mass per unit area of 15 $g/m^2$ and a permeable film having a mass per unit area of 20 $g/m^2$ to each other by a hot-melt adhesive which is applied as a fibrous form in an amount of from 3 $g/m^2$ to 5 $g/m^2$. As the side sheet, an SMS nonwoven fabric having a mass per unit area of 20 $g/m^2$ was used. The hot-melt adhesive to bond the back sheet and the side sheet was applied in an amount of from 5 $g/m^2$ to 20 $g/m^2$. The rupture strength N2 of this sheet was 53.1 N.

In the present invention, preferably, the joining is released before the fastening tape breaks in measuring the joining strength, and the joining strength N1 is lower than the rupture strength N2. When the joining is released before the fastening tape breaks in measuring the joining strength, it means that the joining strength at the joining part is lower than the rupture strength of the fastening tape. When the joining strength N1 is lower than the rupture strength N2, it means that the joining strength at the joining part is lower than the rupture strength of the diaper main body.

The tape substrate may be made of a nonwoven fabric, a woven fabric, a knitted fabric, a plastic film, a laminate of a nonwoven fabric and a plastic film, or the like. Examples of the laminate include, for example, a laminate in which a sheet of a nonwoven fabric and a sheet of a plastic film are stacked, and a laminate in which a plastic film interposed between nonwoven fabrics. The tape substrate is preferably made of a nonwoven fabric or a laminate of a nonwoven fabric and a plastic film from standpoint of easily forming of the joining part. Here, the surface of the laminate on which the joining part is provided is preferably made of a nonwoven fabric.

As the attachment, a hook member and a loop member of a hook-and-loop fastener, an adhesive such as an adhesive tape and an adhesive layer, and the like can be used. When the attachment at the tab part is joined to the adjustment part as shown in FIG. 3, the following combinations of materials of the attachment and the tape substrate are preferred. A hook member is used as the attachment, and a nonwoven fabric or a laminate of a nonwoven fabric and a plastic film is used as a material of the tape substrate. In this case, the surface of the tape substrate to which the attachment is fixed is the nonwoven fabric of the laminate. This is because the surface of the tape substrate having the attachment thereon is the surface to which the attachment is joined when the tab part is folded. Alternatively, an adhesive is used as the attachment, and a plastic film or a laminate of a nonwoven fabric and a plastic film is used as a material of the tape substrate. In this case, the surface of the tape substrate to which the attachment is fixed is the plastic film of the laminate. According to these combinations, the attachment at the tab part is detachably joined to the adjustment part.

A nonwoven fabric used for the tape substrate is preferably a nonwoven fabric manufactured by a spunbond method, an air-through method, a point bonding method, a melt blowing method, an airlaid method, a combination of these methods, or the like. Further, a nonwoven fabric manufactured by the spunbond method or an SMS method which is a combination of the spunbond method and the melt blowing method is preferable, and a nonwoven fabric manufactured by the spunbond method is especially preferable. By using such nonwoven fabrics, the tape substrate with high strength is obtained easily.

A material of the nonwoven fabric used for the tape substrate can be selected as appropriate from synthetic fibers such as polypropylene, polyethylene, polyester and polyamide; natural fibers such as pulp and silk. Among them, synthetic fibers such as polypropylene, polyethylene and polyester are preferable; a polypropylene fiber or a polyester fiber is more preferable. When a nonwoven fabric obtained from such a material is used, a tape substrate with high strength is obtained easily.

The nonwoven fabric used for the tape substrate has preferably a mass per unit area of 30 $g/m^2$ or more, more preferably 50 $g/m^2$ or more, preferably 100 $g/m^2$ or less, and more preferably 85 $g/m^2$ or less. When the nonwoven fabric has a mass per unit area of 30 $g/m^2$ or more, the rupture strength of the fastening tape tends to be larger than the joining strength of the joining part. When the nonwoven fabric has a mass per unit area of 100 $g/m^2$ or less, the nonwoven fabric is easily folded at the adjustment part.

The diaper main body is preferably provided with the attachment-receiving part. The attachment-receiving part is a part or a member to which the attachment of the fastening tape can be joined detachably. For example, when the fastening tape is attached to the front part, the attachment-receiving part is preferably disposed at the back part of the diaper main body. Also, when the fastening tape is attached to the back part, the attachment-receiving part is preferably disposed at the front part of the diaper main body. In wearing the disposable diaper, the fastening tape attached to the back part is joined to the attachment-receiving part disposed at the front part, or the fastening tape attached to the front part is joined to the attachment-receiving part disposed at the back part.

The fastening tape is preferably attached to the diaper main body so that the surface with the attachment faces a wearer. In this case, the attachment-receiving part is preferably disposed on an outer surface, that is an opposite surface of the surface facing a wearer in wearing, of the diaper main body.

The attachment-receiving part is preferably composed of a material to which the attachment can be joined. When the adhesive is used as the attachment, the attachment-receiving part is preferably composed of a plastic film. When the hook member is used as the attachment, the attachment-receiving part is preferably composed of a loop member. The loop member may be composed of a nonwoven fabric, a woven fabric, a knitted fabric, a composite material of a plastic film having a nonwoven fabric, a woven fabric on a surface, or the like. The each material used as the loop member preferably has a loop structure on a surface thereof. In addition, when the attachment-receiving part is disposed on the outer surface of the diaper main body and the back sheet or the outer sheet is composed of a material that serves as the attachment-receiving part, another member which functions as the attachment-receiving part may not be employed.

Next, a material of each member of the disposable diaper of the present invention is explained. The top sheet is preferably composed of a liquid-permeable nonwoven fabric or the like, and the back sheet and the outer sheet are preferably composed of a liquid-impermeable plastic film, a water-repellent nonwoven fabric or the like. The outer sheet may be also composed of a laminate in which a hydrophilic nonwoven fabric and a water-repellent material such as a liquid-impermeable plastic film and a water-repellent nonwoven fabric are stacked.

When the top sheet, the back sheet, or a later-described side sheet is composed of a nonwoven fabric, the nonwoven fabric used for these sheets has preferably a mass per unit area of 5 $g/m^2$ or more, more preferably 10 $g/m^2$ or more, preferably 40 $g/m^2$ or less, and more preferably 35 $g/m^2$ or less. When the nonwoven fabric has a mass per unit area of 5 $g/m^2$ or more, the rupture strength of the diaper main body tends to be larger than the joining strength of the joining part. When the nonwoven fabric has a mass per unit area of 40 $g/m^2$ or less, breathability of the nonwoven fabric is easily ensured, resulting in improving a feel of wearing.

The absorbent core can be obtained, for example, by the steps of: mixing a hydrophilic fiber assembly such as crushed pulp fibers, cellulose fibers and the like with a granular absorbent resin to obtain a clump; wrapping the clump with a paper sheet such as a tissue paper and the like, or with a cover sheet such as a liquid-permeable nonwoven fabric sheet and the like; and molding the obtained wrapped clump into a predefined shape such as a rectangular shape, an hourglass shape, a center nipped-in gourd shape, a battledore shape and the like.

Examples of a bonding means for bonding various members constituting the disposable diaper include an adhesive agent, heat-sealing, ultrasonic sealing, and the like. Examples of the adhesive agent include a hot-melt adhesive such as a polyolefin adhesive, a rubber adhesive, a vinyl acetate adhesive, and the like.

Figure 11:
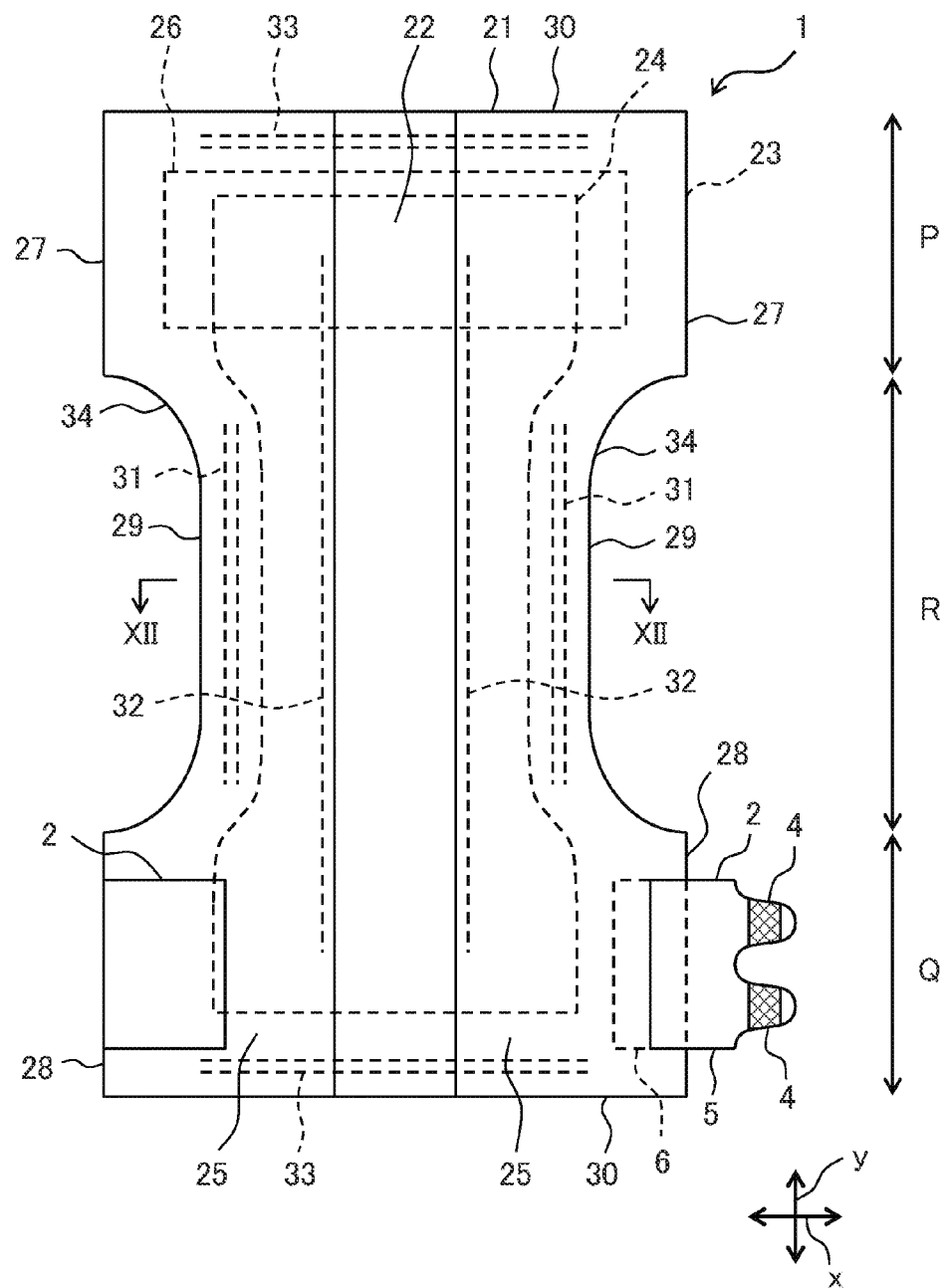
FIG. 11 shows an example of a disposable diaper provided with a fastening tape of the present invention.
Figure 12:
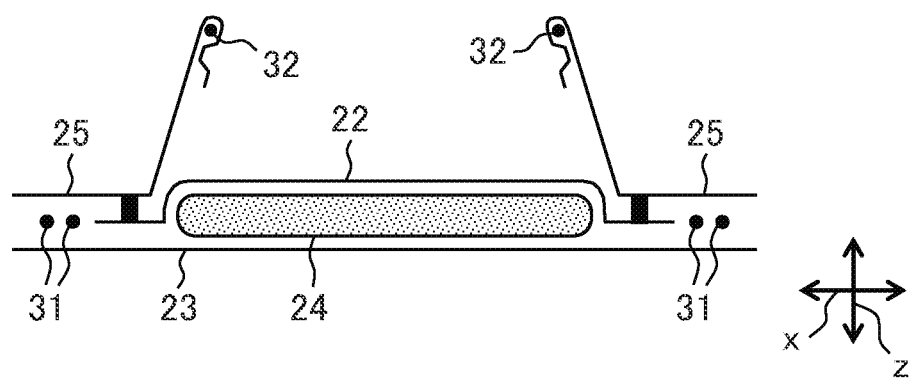
FIG. 12 shows a cross sectional view along line XII-XII in FIG. 11.

An example of the disposable diaper of the present invention is explained, referring to FIGS. 11 and 12. FIG. 11 shows an example of the disposable diaper of the present invention, FIG. 12 shows a cross sectional view along line XII-XII of FIG. 11. In FIGS. 11 and 12, the arrow x direction is defined as a width direction and the arrow y direction is defined as a front-back direction. A vertical direction with regard to a plane formed by the arrows x and y is defined as a vertical direction z (a thickness direction).

A disposable diaper 1 comprises a diaper main body 21 having a front part P, a back part Q and a crotch part R positioned between the front part P and the back part Q. Leg cutout parts 34 are formed at the crotch part R so that a wearer easily steps into the diaper.

The diaper main body 21 comprises a laminate including a liquid-permeable top sheet 22, a liquid-impermeable back sheet 23 and an absorbent core 24 interposed therebetween, and the laminate has the front part P, the back part Q and the crotch part R therebetween. The top sheet 22 is placed so as to face a wearer's skin, and allows excrement such as urine and the like to permeate through. The excrement that permeated the top sheet 22 is accommodated in the absorbent core 24. The back sheet 23 prevents the excrement from leaking outside, thereby protecting clothes and the like becoming soiled.

In FIG. 12, side sheets 25, which extend in the front-back direction y, are provided on left and right side ends, with respect to the width direction x of the disposable diaper 1, of the top sheet 22. The side sheet 25 is joined to an outer end of the top sheet 22. A rising elastic member 32 is disposed at an inner part of the side sheet 25. When the disposable diaper 1 is worn, the inner end of the side sheet 25 rises above the top sheet 22 due to a shrinkage force of the rising elastic member 32. Thus, the inner part of the side sheet 25 rises toward a wearer's skin, thereby preventing excrement such as urine and the like from leaking outward in the width direction x. The side sheet 25 is preferably composed of a liquid-impermeable plastic film, a water-repellent nonwoven fabric or the like, and more preferably composed of a water-repellent nonwoven fabric.

Leg elastic members 31 are disposed between the side sheet 25 and the back sheet 23 in a stretched state along left and right side edges 29 of the crotch part R of the disposable diaper 1. Leg-gathers around wearer's legs are formed due to a shrinkage force of the leg elastic members 31, thereby preventing excrement such as urine and the like from leaking from the crotch part.

A waist elastic member 33 is disposed between the top sheet 22 or the side sheet 25 and the back sheet 23 in a stretched state along an edge 30 in the front-back direction y of the disposable diaper 1. A waist-gather around a wearer's waist is formed due to a shrinkage force of the waist elastic member 33, thereby preventing excrement such as urine and the like from leaking from a back side or an abdomen side.

A pair of fastening tape 2 is attached to left and right side ends 28 of the back part Q of the diaper main body 21. In FIG. 11, the fastening tape 2 is attached between the side sheet 25 and the back sheet 23 at the fixing part 6 so as to extend outward in the width direction x from the disposable diaper 1. An attachment-receiving part 26 is disposed at the front part P. Although it is not shown in FIG. 11, a pair of the fastening tape 2 may be attached to left and right side ends 27 of the front part P, and the attachment-receiving part 26 may be disposed at the back part Q.

The fastening tape 2 attached to the left side end 28 of the back part Q in FIG. 11 (the fastening tape 2 being located on a left side in the drawing and on a left side of a wearer when the diaper is worn) corresponds to a fastening tape in the state shown in the FIG. 4. On the other hand, the fastening tape 2 attached to the right side end 28 of the back part Q in FIG. 11 (the fastening tape 2 being located on a right side in the drawing and on a right side of a wearer when the diaper is worn) corresponds to a fastening tape in the state shown in FIG. 1, that is, in the state where the adjustment part 5 is folded. When the disposable diaper 1 is in an unused state, the fastening tape is preferably in the state shown in the left side of FIG. 11. When the diaper is worn, the fastening tape is preferably in the state shown in the right side of FIG. 11.

Figure 13A:
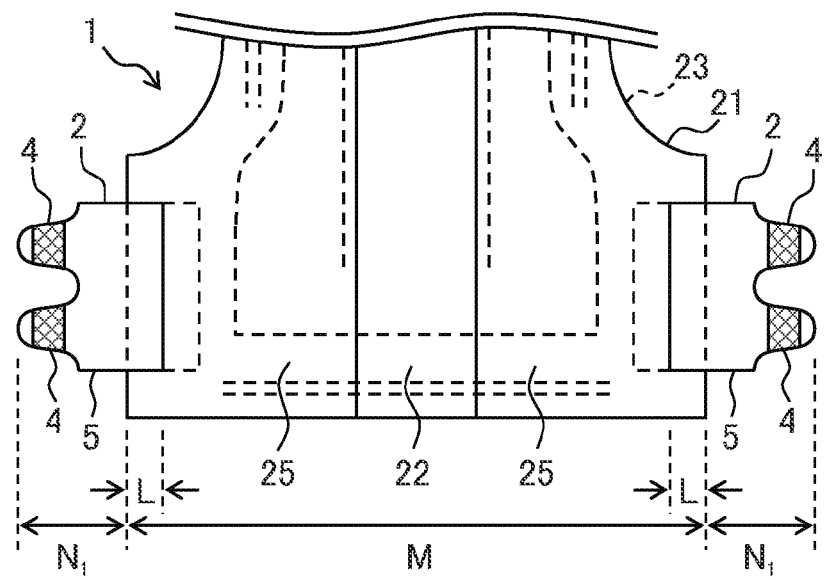
FIG. 13A shows the use of the disposable diaper shown in FIG. 11 in the state where the adjustment part of the fastening tape is folded.

FIG. 13A shows a case where the disposable diaper shown in FIG. 11 is used in a state where the adjustment parts 5 of the fastening tapes 2 attached to the left and right side ends 28 are folded. In the disposable diaper 1 shown in FIG. 13A, the length of the diaper main body 21 in the width direction is M, and the length from the outer edge of the diaper main body 21 to the end of each fastening tape 2 is $N_1$. In one fastening tape 2, the adjustment part 5 is folded for a length of 2L. In the state where the adjustment part 5 is folded, a wearer's waist on the back side is covered with the back part Q of the disposable diaper 1 by a length of $M+2N_1$.

Figure 13B:
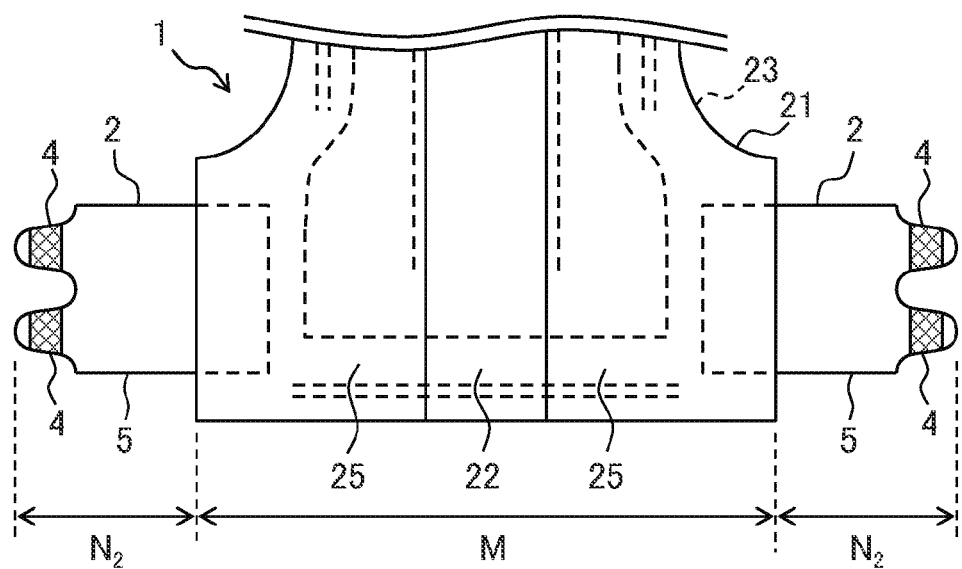
FIG. 13B shows the use of the disposable diaper shown in FIG. 11 in the state where the adjustment part of the fastening tape is unfolded.

FIG. 13B shows a case where the disposable diaper shown in FIG. 11 is used in a state where the adjustment parts 5 of the fastening tapes 2 attached to the left and right side ends 28 are unfolded. In the disposable diaper 1 shown in FIG. 13A, the length of the diaper main body 21 in the width direction is M, and the length from the outer edge of the diaper main body 21 to the end of each fastening tape 2 is $N_2$. Here, the equality: $N_2=N_1+2L$ is satisfied. In the state where the adjustment part 5 is unfolded, the wearer's waist on the back side is covered with the back part Q of the disposable diaper 1 by a length of M+2N$_2$. Thus, in the state where the adjustment part 5 is unfolded, the length for covering the waist increases by a length of 4L as compared to that in the state where the adjustment part 5 is folded. Therefore, in the disposable diaper of the present invention, since the fastening tape is adjustable its length by folding or unfolding the adjustment part in accordance with the size of the wearer's waist, the disposable diaper of one size can be worn by people of various body types.

REFERENCE SIGNS LIST

1: a disposable diaper
2: a fastening tape
3: a tape substrate
4: a tab part
5: an adjustment part
6: a fixing part
9: an attachment
11: a joining part
21: a diaper main body
26: an attachment-receiving part

The invention claimed is:

1. A disposable diaper comprising:
a fastening tape having a tab part which is formed at one end of a tape substrate, a fixing part which is formed at the other end of the tape substrate, and an adjustment part which is formed between the tab part and the fixing part;
a diaper main body having a front part, a back part and a crotch part positioned between the front part and the back part; and
an attachment fixed to the tab part;
wherein:
the fastening tape is attached to a side end of the front or back part of the diaper main body at the fixing part;
the adjustment part has a joining part, the adjustment part having a folded state and an unfolded state, the adjustment part in the folded state being folded and temporarily joined to the diaper main body and/or the fastening tape at the joining part, the adjustment part in the unfolded state being unfolded, the temporary joining of the adjustment part at the joining part being releasable to bring the adjustment part from the folded state to the unfolded state;
the attachment is located entirely outside the diaper main body when the fastening tape is used, both when the adjustment part is in the folded state and in the unfolded state; and
the disposable diaper is wearable both when the adjustment part is in the folded state and in the unfolded state.

2. The disposable diaper according to claim 1, wherein the adjustment part extends from an outer border of the fixing part in a width direction of the disposable diaper.

3. The disposable diaper according to claim 1, wherein the joining part is formed by an adhesive.

4. The disposable diaper according to claim 1, wherein the joining part is formed by heat-sealing.

5. The disposable diaper according to claim 3, wherein the joining part is provided discontinuously.

6. The disposable diaper according to claim 1, wherein a joining strength at the joining part is lower than rupture strengths of the diaper main body and the fastening tape.

7. The disposable diaper according claim 1, wherein the tab part is turned back by folding the adjustment part at a fold so that the attachment is inside the fold, and the attachment is joined to the adjustment part.

8. The disposable diaper according to claim 4, wherein the joining part is provided discontinuously.

9. The disposable diaper according to claim 1, wherein the adjustment part is folded and temporarily joined to the diaper main body at the joining part.

10. The disposable diaper according to claim 1, wherein a length of the fastening tape between the attachment and the joining part which is the nearest to the attachment is longer than a length between an outer edge of the diaper main body and the joining part which is the nearest to the attachment.

11. The disposable diaper according to claim 1, wherein the fixing part is fixed to the diaper main body.

12. The disposable diaper according to claim 1, wherein the adjustment part is folded inwardly and the inwardly-folded adjustment part is folded outwardly.

13. The disposable diaper according to claim 1, wherein:
the fastening tape is attached to the side end of the back part of the diaper main body at the fixing part, and
the disposable diaper further comprises an attachment-receiving part provided at the front part of the diaper main body, the attachment of the fastening tape being detachably joinable to the attachment-receiving part.

14. The disposable diaper according to claim 1, wherein a length of the fastening tape is adjustable by folding or unfolding the adjustment part.

15. The disposable diaper according to claim 1, wherein the attachment is a hook member of a hook-loop-fastener.

* * * * *